United States Patent
Isola et al.

(10) Patent No.: US 11,147,985 B2
(45) Date of Patent: Oct. 19, 2021

(54) WARM START INITIALIZATION FOR EXTERNAL BEAM RADIOTHERAPY PLAN OPTIMIZATION

(71) Applicant: KONINKLIJKE PHILIPS N.V., Eindhoven (NL)

(72) Inventors: Alfonso Agatino Isola, Eindhoven (NL); Christoph Neukirchen, Aachen (DE); Torbjoern Vik, Hamburg (DE); Harald Sepp Heese, Hamburg (DE); Rolf Juergen Weese, Nordersteft (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/481,998

(22) PCT Filed: Jan. 24, 2018

(86) PCT No.: PCT/EP2018/051759
§ 371 (c)(1),
(2) Date: Jul. 30, 2019

(87) PCT Pub. No.: WO2018/141606
PCT Pub. Date: Aug. 9, 2018

(65) Prior Publication Data
US 2019/0388709 A1    Dec. 26, 2019

(30) Foreign Application Priority Data

Feb. 2, 2017  (EP) .................................... 17154324

(51) Int. Cl.
*A61N 5/10*    (2006.01)

(52) U.S. Cl.
CPC ............. *A61N 5/1031* (2013.01); *A61N 5/10* (2013.01); *A61N 5/103* (2013.01); *A61N 5/1042* (2013.01);
(Continued)

(58) Field of Classification Search
CPC ........ A61N 5/10; A61N 5/103; A61N 5/1031; A61N 5/1036; A61N 5/1042; A61N 5/1045; A61N 5/1047
(Continued)

(56) References Cited

U.S. PATENT DOCUMENTS 5,818,902 A * 10/1998 Yu .................. A61N 5/1047
                                                    378/65
6,504,899 B2 * 1/2003 Pugachev .......... A61N 5/103
                                                    378/65
(Continued)

FOREIGN PATENT DOCUMENTS

WO    2008039991 A1    4/2008

OTHER PUBLICATIONS

Unkelbach, Jan et al "Optimization Approaches to Volumetric Modulated ARC Therapy Planning", Medical Physics, vol. 42, No. 3, Mar. 2015, pp. 1367-1377.
(Continued)

*Primary Examiner* — Allen C. Ho

(57) ABSTRACT

The invention relates to a dynamic sliding-window-like initialization for, for example, iterative VMAT algorithms. Specifically, a dynamic sliding window conversion method is contemplated where typical dynamic VMAT constraints are taken into account to find an optimal set of suitable openings (i.e. binary masks) that can be used as quasi-feasible start initialization for any VMAT algorithm that can refine until a deliverable plan is reached. Here, a multileaf leaf tip trajectory least square constrained optimization is performed to find a set of optimal unidirectional trajectories for all MLC leaf pairs of all arc points. To ensure that a quasi-feasible (or better quasi-deliverable) solution is returned, for example, a maximum dose rate, a maximum
(Continued)

gantry speed, a maximum leafs speed, and a maximum treatment time may be enforced.

20 Claims, 8 Drawing Sheets

(52) U.S. Cl.
CPC ......... *A61N 5/1045* (2013.01); *A61N 5/1047* (2013.01); *A61N 5/1036* (2013.01)

(58) Field of Classification Search
USPC .......................................................... 378/65
See application file for complete search history.

(56) References Cited

U.S. PATENT DOCUMENTS

| | | | | |
|---|---|---|---|---|
| 6,735,277 B2* | 5/2004 | McNutt | A61N 5/1031 | 378/64 |
| 7,085,348 B2* | 8/2006 | Kamath | A61N 5/103 | 378/65 |
| 7,180,980 B2* | 2/2007 | Nguyen | A61N 5/103 | 378/148 |
| 7,496,173 B2* | 2/2009 | Goldman | G06F 19/3481 | 378/65 |
| 7,519,150 B2* | 4/2009 | Romesberg, III | A61N 5/1031 | 378/64 |
| 7,590,219 B2* | 9/2009 | Maurer, Jr. | A61N 5/103 | 378/145 |
| 7,734,010 B2* | 6/2010 | Otto | A61N 5/1031 | 378/65 |
| 7,801,270 B2* | 9/2010 | Nord | A61N 5/1031 | 378/65 |
| 7,831,289 B2* | 11/2010 | Riker | A61N 5/1031 | 600/407 |
| 7,835,493 B2* | 11/2010 | Keall | A61N 5/1042 | 378/65 |
| 7,839,974 B2* | 11/2010 | Shepard | A61N 5/1047 | 378/65 |
| 7,880,154 B2* | 2/2011 | Otto | A61N 5/1049 | 250/505.1 |
| 7,906,770 B2* | 3/2011 | Otto | A61N 5/1031 | 250/492.3 |
| 8,009,804 B2* | 8/2011 | Siljamaki | A61N 5/1031 | 378/65 |
| 8,014,494 B2* | 9/2011 | Yu | A61N 5/1047 | 378/65 |
| 8,073,103 B2* | 12/2011 | Otto | A61N 5/1038 | 378/65 |
| 8,077,936 B2* | 12/2011 | Wang | A61N 5/103 | 382/128 |
| 8,180,020 B2* | 5/2012 | Kilby | A61N 5/10 | 378/65 |
| 8,222,616 B2* | 7/2012 | Lu | A61N 5/103 | 250/491.1 |
| 8,295,436 B2* | 10/2012 | Nord | A61N 5/1036 | 378/65 |
| 8,315,357 B2* | 11/2012 | Zhu | A61N 5/1031 | 378/65 |
| 8,331,532 B2* | 12/2012 | Nord | G21K 1/046 | 378/65 |
| 8,363,784 B2* | 1/2013 | Sobering | A61N 5/1031 | 378/65 |
| 8,401,148 B2* | 3/2013 | Lu | A61N 5/1045 | 378/65 |
| 8,615,068 B2* | 12/2013 | Gunawardena | A61N 5/1036 | 378/65 |
| 8,961,382 B2* | 2/2015 | Nord | A61N 5/1031 | 600/1 |
| 8,971,489 B2* | 3/2015 | Ruan | A61N 5/1031 | 378/65 |
| 8,986,186 B2* | 3/2015 | Zhang | A61N 5/103 | 600/1 |
| 9,020,234 B2* | 4/2015 | Netsch | G06T 7/0012 | 382/131 |
| 9,251,302 B2* | 2/2016 | Brand | A61N 5/1031 | |
| 9,289,627 B2* | 3/2016 | Otto | A61N 5/00 | |
| 9,393,442 B2* | 7/2016 | Isola | A61N 5/1047 | |
| 9,421,397 B2* | 8/2016 | Purdie | A61N 5/103 | |
| 9,443,633 B2* | 9/2016 | Orton | G21K 1/046 | |
| 9,468,776 B2* | 10/2016 | Fredriksson | A61N 5/1031 | |
| 9,504,850 B2* | 11/2016 | Zhang | A61N 5/1049 | |
| 9,507,886 B2* | 11/2016 | Fiege | G06F 30/20 | |
| 9,782,607 B2* | 10/2017 | Wiersma | A61N 5/1031 | |
| 9,925,393 B2* | 3/2018 | Nakatsugawa | A61B 6/06 | |
| 10,039,936 B2* | 8/2018 | Nord | A61N 5/1031 | |
| 10,076,673 B2* | 9/2018 | Ranganathan | A61N 5/1077 | |
| 10,143,859 B2* | 12/2018 | Ollila | A61N 5/1031 | |
| 10,272,264 B2* | 4/2019 | Ollila | A61N 5/1042 | |
| 10,279,196 B2* | 5/2019 | West | A61N 5/1031 | |
| 10,279,197 B2* | 5/2019 | Nord | A61N 5/1031 | |
| 10,307,614 B2* | 6/2019 | Schnarr | A61N 5/1031 | |
| 10,307,615 B2* | 6/2019 | Ollila | A61N 5/103 | |
| 10,417,390 B2* | 9/2019 | Svatos | G06N 7/005 | |
| 10,441,812 B2* | 10/2019 | Bokrantz | A61N 5/1071 | |
| 10,449,389 B2* | 10/2019 | Ollila | A61N 5/1036 | |
| 10,456,103 B2* | 10/2019 | Bose | A61N 5/1036 | |
| 10,485,988 B2* | 11/2019 | Kuusela | A61N 5/103 | |
| 10,525,283 B2* | 1/2020 | MacDonald | A61N 5/103 | |
| 10,537,749 B2* | 1/2020 | Isola | A61N 5/1031 | |
| 10,549,115 B2* | 2/2020 | Papp | A61N 5/1081 | |
| 10,549,116 B2* | 2/2020 | Sheng | A61N 5/1047 | |
| 10,549,120 B2* | 2/2020 | Eriksson | G16H 50/20 | |
| 10,617,887 B2* | 4/2020 | Ranganathan | A61N 5/1031 | |
| 10,639,501 B2* | 5/2020 | Peltola | A61N 5/103 | |
| 10,918,884 B2* | 2/2021 | O'Connor | A61N 5/1039 | |
| 10,987,523 B2* | 4/2021 | Sheng | A61N 5/1036 | |
| 2006/0045238 A1 | 3/2006 | Nguyen | | |
| 2006/0256915 A1 | 11/2006 | Otto | | |
| 2008/0123813 A1 | 5/2008 | Maurer | | |
| 2009/0225942 A1 | 9/2009 | Shepard | | |
| 2013/0077751 A1 | 3/2013 | Gunawardena | | |

OTHER PUBLICATIONS

International Search Report for PCT/EP2018/051759, dated May 18, 2018.
Otto, K. "Volumetric modulated ARC Therapy: IMRT in a Single Gantry ARC", Medical Physics, vol. 35, No. 1, 2008, pp. 310-317—Abstract.
Bzdusek, K. "Development and Evaluation of an Efficient Approach to Volumetric ARC Therapy Planning", Medical Physics, vol. 36, No. 6, 2009, pp. 2328-2339. Abstract.
Feygelman, V. et al "Initial Dosimetric Evaluation of SmartARC—a Novel VMAT Treatment Planning Modular Implemented in a Multi-Vendor Delivery Chain", Journal of Applied Clinical Medical Physics, vol. 11, No. 1, Jan. 2010.
Webb, S. et al "Some Considerations concerning Volume-Modulated ARC Therapy: a Stepping Stone Towards a General Theory", Physics Medical Biology, vol. 54, No. 14, 2009, pp. 4345-4360.
Korreman, S. et al "Dosimetric Verification of RapidARC Treatment Delivery", Acta ONCOL. vol. 48, No. 2, 2009, pp. 185-191.
Younge, K.C. et al "Penalization of Aperture Complexity in Inversely Planned VMAT", Medical Physics, vol. 39, No. 11, Nov. 2012.
Nicolini, G. et al "The GLASaS Algorithm for Portal Dosimetry and Quality Assurance of RapidARC, an Intensity Modulated Rotational Therapy", Radiation Oncology, vol. 3, No. 24, 2008.
Kamath, S. et al "Leaf Sequencing Algorithms for Segmented Multileaf Collimation", Physics Medical Biology, vol. 48, No. 3, 2003, pp. 307-324.
Webb, S. "Configuration Options for Intensity Modulated Radiation Therapy using Multi-Static Fields Shaped by a Multileaf Collimator", Physics Medical Biology, vol. 43, 1998, pp. 241-260. Abstract.
Ben-Tal, A. et al "Penalty Barrier Multiplier Methods for Convex Programming Problems", SIAM Journal of Optimization, vol. 7, 1997, pp. 347-366.

(56) References Cited

OTHER PUBLICATIONS

Craft, David et al "Plan Averaging for Multicriteria Navigation of Sliding Window IMRT and VMAT", Medical Physics, vol. 41, No. 2, Feb. 2014, pp. 021709-1-021709-5.

* cited by examiner (A)　(B)

WARM START INITIALIZATION FOR EXTERNAL BEAM RADIOTHERAPY PLAN OPTIMIZATION

FIELD OF THE INVENTION

The present invention relates to planning of external beam radiotherapy (in particular volumetric modulated arc therapy (VMAT)) with a multileaf collimator (MLC) and particularly to an approach of generating an input for optimization of an external beam radiotherapy plan, so to provide a warm start initialization of the optimization.

BACKGROUND OF THE INVENTION

In order to implement VMAT, as an example of external beam radiotherapy, safely and efficiently, it is important to understand the characteristics of MLCs, the associated delivery systems, and the limitations of each system when applied to VMAT.

Conventionally, starting with a limited number of "ideal" intensity distributions (ideal fluence maps) computed at typically equispaced angular positions along the whole VMAT arc, an initial set of optimal arc MLC segment openings (also referred to as "control points") are created. In order to reach the user required dose quality, these arc openings are further refined via multiple subsequent dose optimizations which mainly aim to reduce both the leaf tips scattering effect and the geometrical discretization error (dose angular approximation) that is introduced when using only few fluence maps optimized at very limited VMAT arc angular positions.

Several approaches have been proposed in literature for VMAT arc opening generation (AOG), i.e. arc leaf sequencing (see, for example, "Volumetric modulated arc therapy: IMRT in a single gantry arc" by K. Otto (Med Phys. 2008; 35(1); 310-17), "Development and evaluation of an efficient approach to volumetric arc therapy planning" by K. Bzdusek (Med Phys. 2009; 36(6); 2328-39) or "Optimization approaches to volumetric modulated arc therapy planning" by J. Unkelbach et al. (Med. Phys. 42, 1367 (2015)).

In general these methods try to create a discretized set of arc segment openings able to continuously deliver an optimal dose distribution that satisfies all clinical constraints. In order to ensure deliverability, static and dynamic machine constraints are also taken into account during the VMAT plan optimization.

A well-known VMAT discretization issue is known as "small arc approximation error" (see, for example, "Initial dosimetric evaluation of SmartArc—a novel VMAT treatment planning module implemented in a multi-vendor delivery chain" by V. Feygelman et al. (Journal of Applied Clinical Medical Physics, v. 11, n. 1, January 2010) or "Some considerations concerning volume-modulated arc therapy: a stepping stone towards a general theory" by S. Webb and D. McQuaid (Phys Med Biol. 2009; 54(14):4345-60)). This is the dose error produced when a discrete arc is optimized and delivered instead of an ideal continuous VMAT arc. Webb and McQuaid first described and formalized this concept, and pointed out that the approximation breaks down as the point of interest moves away from the isocenter.

The dose inaccuracy and its related plan quality degradation is typically observed and measured during the planning QA stage. Usually, a VMAT arc linear interpolation is applied to artificially reduce control point's angular spacing and a final dose distribution is measured over the interpolated arc. Commonly, a big plan quality degradation is observed in the cases where segment opening shapes rapidly change along the arc (see Feygelman), or in the cases where openings shapes were pretty snaky and/or jagged (see, for example, "Dosimetric verification of RapidArc treatment delivery" by S. Korreman et al. (Acta Oncol. 2009; 48(2): 185-91), "Penalization of aperture complexity in inversely planned VMAT" by K. C. Younge et al. (Medical Physics, Vol. 39, No. 11, November 2012) or "The GLAaS algorithm for portal dosimetry and quality assurance of RapidArc, an intensity modulated rotational therapy" by G. Nicolini et al. (Radiation Oncology 2008 3:24)). Highly jagged shapes of the irradiated area, with regions presenting alternate open and closed leaves enhances the role of small discrepancies between measurements and calculations of leaf edge penumbra due to the different spatial resolutions (see FIG. 1(A)-(B)), which are taken from the papers of Nicolini et al. and Younge et al., with FIG. 1(A) illustrating a measured dose (A, top; GLAsS algorithm) and gamma index evaluation between measured and calculated doses (A, bottom) for an arc with 6 degrees equally spaced control points (left: CP 2-5, middle: CP 5-8; right: CP 8-11) and FIG. 1(B) giving a calculated-measured dose difference image for one arc control point).

In literature it was shown that having arc segment openings of large size, symmetric to the isocenter, and smoothly changing their shapes along the arc could lead to an improved dosimetric accuracy (see, for example, Feygelman). As a direct consequence, in practice, control points openings that are large, (potentially) symmetric with respect to the isocenter, and smoothly changing along the arc are the most favorable to reduce discrepancies between planned and measured dose distributions.

SUMMARY OF THE INVENTION

It is an object of the present invention to provide an approach for (further) improving the dose quality and robustness of the outcome of external beam radiotherapy (e.g. VMAT) plan optimization (i.e. the dose quality and robustness of the final optimized external beam radiotherapy (e.g. VMAT) plan).

In a first aspect of the present invention, a computer-implemented method of generating an input for an optimization of a external beam radiotherapy plan for a multileaf collimator is presented, comprising an information obtainment step of obtaining information indicative of a desired dosage and/or intensity distribution, an optimization step of solving, for each of a plurality of arc angular sectors or positions, a constrained optimization problem, so to obtain leaf tip trajectories or positions reflecting the desired dosage and/or intensity distribution, the constraints including constraints as to an energy source, static constraints as to the multileaf collimator and/or dynamic constraints as to the multileaf collimator, and a calculation step of calculating, for each of the plurality of the arc angular sectors or positions, a binary mask indicating exposure of bixels by the multileaf collimator, wherein the plurality of binary masks are made available as input for the optimization of the external beam radiotherapy plan.

In a second aspect of the present invention, a device for generating an input for an optimization of a external beam radiotherapy plan for a multileaf collimator is presented, comprising an information obtainment unit for obtaining information indicative of a desired dosage and/or intensity distribution, an optimization unit for solving, for each of a plurality of arc angular sectors or positions, a constrained optimization problem, so to obtain leaf tip trajectories or positions reflecting the desired dosage and/or intensity distribution, the constraints including constraints as to an energy source, static constraints as to the multileaf collimator and/or dynamic constraints as to the multileaf collimator, and a calculation unit for calculating, for each of the plurality of the arc angular sectors or positions, a binary mask indicating exposure of bixels by the multileaf collimator, wherein the device is arranged to make available the plurality of binary masks as input for the optimization of the external beam radiotherapy plan.

The present invention relates to a dynamic sliding-window-like initialization for, for example, iterative VMAT algorithms.

In the case of VMAT (or the like) a plurality of arc angular sectors is considered and leaf tip trajectories are obtained.

An aim of the inventors is to propose a new dynamic sliding window technique (see, for example, "*Leaf Sequencing Algorithms for Segmented Multileaf Collimation*" by S. Kamath et al. (Phys Med Biol, 2003, 48(3):307-24) or "*Configuration options for intensity modulated radiation therapy using multi-static fields shaped by a multileaf collimator*" by S. Webb (Phys Med Biol, 1998, 43:241-60)) that can provide an initial "quasi deliverable" set of moderately large and smoothly changing arc control point openings. These control point openings can be used as warm start initialization for, for example, a VMAT refinement approach.

It was found that the resulting reduced complexity of the segment openings shapes and the smoother leaf tips movement along the VMAT arc points produced by such a sliding window warm start initialization technique can help to strongly improve the dose quality and robustness of the final optimized VMAT plan.

The delivery of volumetric modulated arc therapy (VMAT) with a multileaf collimator (MLC) typically includes the conversion of radiation fluence maps optimized at a number of angular arc positions into a leaf sequence file that controls the movement of the MLC, the gantry speed and the dose rate of the linac during radiation delivery.

Due to the well-known VMAT "small arc approximation error" minimal deviations between planned and measured dose distributions are observed at subsequent quality assurance (QA) plan tests. In literature it was shown that in average less complex (i.e. more regularly shaped) and larger arc segment openings smoothly changing their shapes along the VMAT arc points can strongly reduce the observed deviation between calculated and measured dose distributions.

Improvements to the leaf sequencing algorithm for VMAT has been the subject of several recent investigations. Leaf sweeping (aka dynamic sliding window) sequencing has been shown to provide optimal arc openings with gradually and smoothly changing segment shapes from arc point to arc point, and ensuring minimum leaf movement. Nevertheless, in the standard sliding window conversion approach, typical dynamic VMAT constraints are not considered, leading to suboptimal initialization of further VMAT processing steps and suboptimal VMAT results after optimization.

Here, a dynamic sliding window conversion method is contemplated where typical dynamic VMAT constraints are taken into account to find an optimal set of suitable openings (i.e. binary masks) that can be used as quasi-feasible start initialization for any VMAT algorithm that can refine until a deliverable plan is reached. Here, a multileaf leaf tip trajectory least square constrained optimization is performed to find a set of optimal unidirectional trajectories for all MLC leaf pairs of all arc points. To ensure that a quasi-feasible (or better quasi-deliverable) solution is returned, for example, a maximum dose rate, a maximum gantry speed, a maximum leafs speed, and a maximum treatment time may be enforced.

The reduced complexity of the segment openings shapes and the smooth leaf tips movement along the VMAT arc points produced by such a quasi-feasible sliding window warm start initialization technique can help to strongly improve the dose quality and robustness of the final optimized VMAT plan.

The present invention is not limited to the field of VMAT and can be, for example, applied also in the field of "step & shoot" static beams intensity modulated radiation therapy (IMRT) delivery, as well as other external beam radiotherapy approaches.

With static beams IMRT, after fluence map optimization, a set of 2D fluence maps may be computed for a limited number of beams, while, further, a number of static MLC openings are computed to model every fluence map of each static beam (also referred to as leaf sequencing, conversion or segmentation step).

In this context, the present invention can be used to generate a set of quasi feasible openings to initialize the static MLC openings generation process (e.g, direct machine parameter optimization (DMPO) and/or leaf sequencing algorithm).

In a further aspect of the present invention a computer program is presented for generating an input for an optimization of a volumetric modulated arc therapy plan for a multileaf collimator, the software product comprising program code means for causing a computer to carry out the steps of the method of the invention when the software product is run on the computer.

It shall be understood that the claimed method, device, and computer program have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
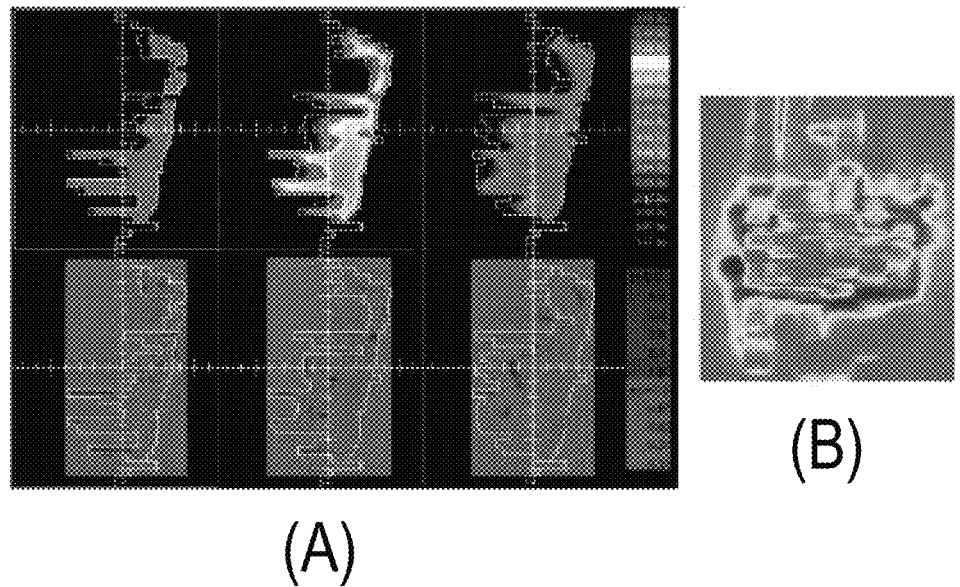
FIGS. 1 (A) and (B) show a measured dose and gamma index evaluation and a calculated-measured dose image difference for one arc control point.

FIGS. 1 (A) and (B) show a measured dose and gamma index evaluation and a calculated-measured dose image difference for one arc control point and are briefly discussed above.

Figure 2:
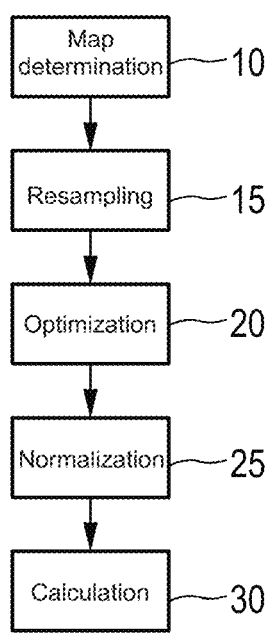
FIG. 2 shows a flow diagram illustrating a method in accordance with an embodiment of the invention, FIG. 3 (A) shows an example of leaf tip trajectories tip for an MLC leaf pair (row), FIG. 3 (B) illustrate sketchwise an angular sector shared by one fluence map.

FIG. 2 shows a flow diagram illustrating a method in accordance with an embodiment of the invention.

In a fluence map determination step 10, a set of N fluence maps is determined for each VMAT arc angular sector (typically for a 360 degree arc, N=15 fluence maps are optimized for every 24 degree equally spaced angular sector).

Given a user-defined VMAT arc, a set of N 2D target fluence maps is determined for each VMAT arc angular sector. The optimal fluence maps are calculated by solving a positivity-constrained optimization problem with known methods.

In a following resampling step 15, ideal 2D fluence maps are resampled to fit the specific linac (linear accelerator) MLC grid resolution.

The 2D target fluence maps and the MLC grids may be given (and are typically given) in different coordinate systems. Hence, to be actually delivered, the ideal fluence matrix must be geometrically transformed to match the MLC geometry. This task can be easily performed using a multitude of resampling approaches. One possible solution might be to average the pixels intensities along the leaf widths, this defines a new matrix that is consistent with the leaf widths, and thus in principle deliverable. Moreover, geometrical transformations (e.g. MLC tilting) could be needed in order to exactly match the MLC grid orientation. Optionally, an additional low-pass filtering can be applied to reduce the noise possibly present in the target fluence map.

It may be noted that steps like steps 10 and 15 are already conventionally used in typical VMAT inverse planning, so that the skilled person is already familiar with such aspects of the described method, while these steps may be considered as an example of an information obtainment step, insofar as the resampled fluence maps are indicative of the desired intensity distribution.

Further, in an optimization step 20, for each fluence map the best set of quasi-feasible MLC leaf tips trajectories optimally modeling the fluence map profiles is computed by minimizing a least-square constrained optimization problem. Here it may be that only a limited number of static and dynamic MLC and linac machine constraints are taken into account.

A set of binary masks (one per arc control point) is computed, in calculation step 30, from the set of optimal trajectories computed at the previous optimization step 20 and normalized in a normalization step 25.

Finally, this set of binary masks can be used as warm start initialization for a subsequent VMAT method (not shown).

In the present embodiment, in the optimization step 20, for each resampled 2D fluence map (resulting from the resampling step 15) a least squares function is minimized to find the best set of left and right leaf tips trajectories modeling the current fluence map.

Figure 3:
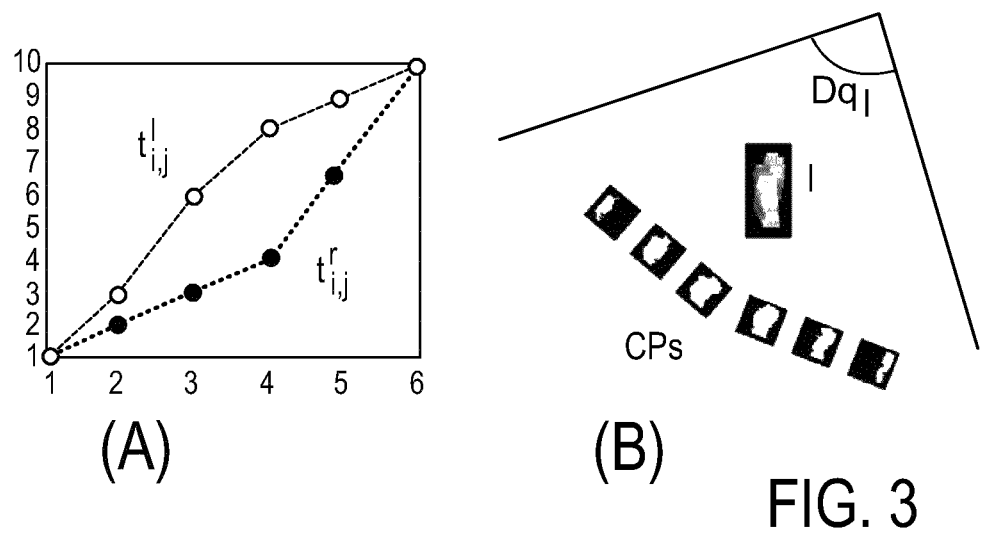

Commonly, in the dynamic sliding window conversion (as discussed, for example by S. Kamath et al. or S. Webb, see above) the leaf tips trajectories are given in a spatio-temporal space (see FIG. 3(A), showing an example of trajectories of a left leaf tip (dashed line) and a right leaf tip (dotted line) for an MLC leaf pair (row) with bixel as abscissa and time as ordinate). For example, if a unidirectional leaf tip movement from left to right is performed, the leaf tip trajectories describe the total exposure time of a specific bixel from the time it is exposed by the right leaf tip to the time it is successively covered by the corresponding left leaf tip. The total exposure time of a bixel multiplied by a linac dose rate value will give a direct indication of the amount of MU (monitor units) that is going to be delivered via that specific bixel. In the standard dynamic sliding window technique, as discussed, for example by S. Kamath et al. or S. Webb, typical dynamic VMAT constraints are not taken into account potentially leading to suboptimal VMAT plans.

In the present embodiment a linearly constrained optimization problem is solved where the best set of unidirectional moving trajectories for all MLC leaf pairs is found such that the similarity distance to the fluence map is minimized in a least squares sense:

$$\min_{t^l_{i,j}, t^r_{i,j}} \sum_{i=0}^{NRows-1} \sum_{j=0}^{NCols-1} [I(i,j) - r*(t^l_{i,j} - t^r_{i,j})]^2 \quad (P)$$

s.t.

$$t^l_{i,j} \geq t^l_{i,j-1} + \frac{1}{s_{leaf}}$$

$$t^r_{i,j} \geq t^r_{i,j-1} + \frac{1}{s_{leaf}}$$

$$t^l_{i,j} \geq t^r_{i,j}$$

$$0 \leq t^l_{i,j} \leq t_{max}$$

$$0 \leq t^r_{i,j} \leq t_{max}$$

$$t_{max} = \frac{\Delta \theta_l}{S_{gantry}}$$

$i = 0, \ldots, NRows$ (leaf pairs index)

$j = 0, \ldots, NCols$ (bixels index)

The first two constraints provide for unidirectional leaf tip motions and the trajectory slope, while the third constraint provides for an avoiding of leaf tips crashing. Here I(i, j) is the current fluence map value (MU) at the i-th row (i.e., leaf pair index) and j-th column (i.e., bixel), $t_{i,j}^r$ and $t_{i,j}^l$ indicate the time at which the i-th left and right leaf tips expose and successively cover the j-th bixel, respectively (see FIG. 3(A)). A maximum treatment time $$t_{max} = \frac{\Delta \theta_l}{S_{gantry}}$$

is enforced as time upper bound to ensure leaf tip trajectories are deliverable within an acceptable amount of time (see FIG. 3(B), illustrating sketchwise an angular sector shared by one fluence map I). Moreover, dose rate r, gantry speed $S_{gantry}$, and leaf speed $S_{leaf}$ maximum values are given and taken into account to ensure a minimum trajectory slope during optimization. Finally, linear constraints are also enforced to ensure a unidirectional leaf tip movement, a minimum trajectory slope, and to avoid leaf tips crashing (see FIG. 4, discussed below).

For static beams delivery, e.g. in the context of IMRT as discussed above, the constrained problem at (P) may be simplified by removing the $t_{max}$ upper bound since no maximum treatment time needs to be enforced during static beam delivery.

The constrained problem at (P), as the skilled person appreciates, can be minimized using every kind of constrained solver available in literature (see, for example, "Penalty barrier multiplier methods for convex programming problems" by A. Ben-Tal et al. (SIAM Journal of Optimization, 1997, vol. 7, pp. 347-366)). Moreover, even if the amount of linear constraints can be very huge, thanks to Jacobian matrix sparsity, the actual amount of matrix-vector multiplications can be strongly reduced.

The problem (P) might potentially have multiple equivalent optimal solutions (i.e. leaf tips trajectories) satisfying all constraints. Hence a smart trajectories initialization could be a way to prefer some specific features on the final optimal trajectories/solution. A possible approach includes setting initial trajectories (naively) all to zero, or one could initialize them with some leaf sweeping trajectories (even fully unfeasible) obtained via other different approaches (see, for example, S. Kamath et al. or S. Webb).

Figure 4:
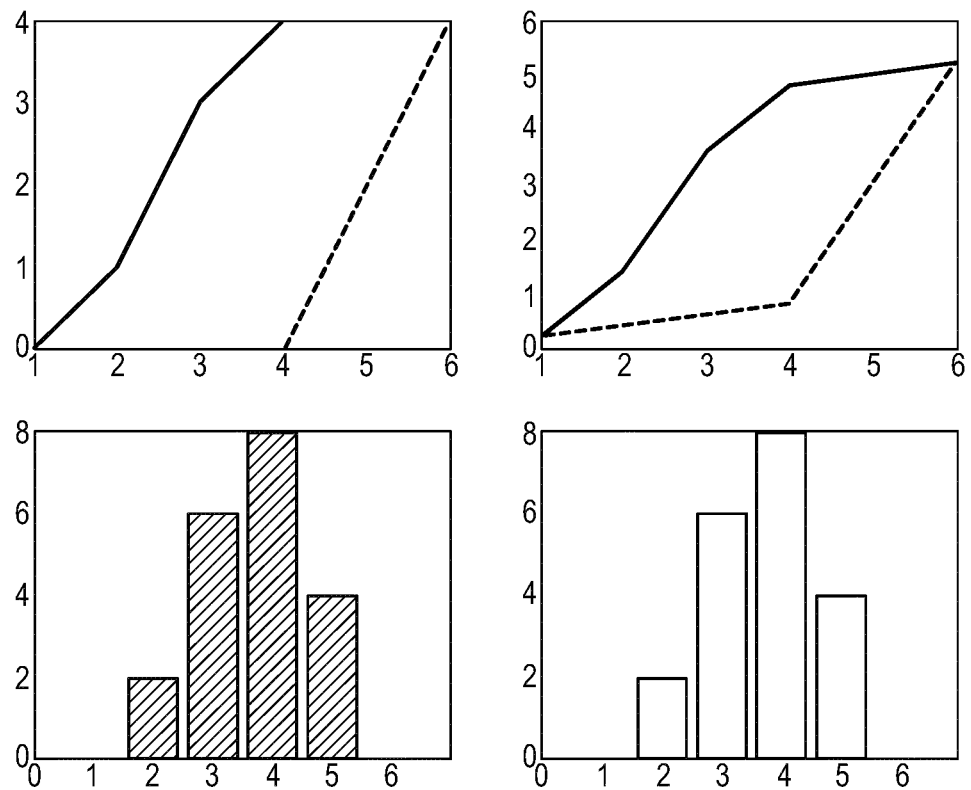
FIG. 4 illustrates ideal trajectories of leaf tips, a 1D fluence map profile and a modeled profile.

FIG. 4 illustrates ideal trajectories of leaf tips, a 1D fluence map profile and a modeled profile. In the top portion of FIG. 4, ideal trajectories where infinite leaf speed is assumed (left) and corresponding leaf trajectories where a minimum slope is enforced (right) are shown (bixel as abscissa and time as ordinate). In the bottom part of FIG. 4, the 1D fluence map profile (left) and the corresponding modeled profile (right) are shown (bixel as abscissa and monitor units (MU) as ordinate). Both trajectories on top are able to reproduce the very same modeled fluence map profile (bottom, right) since adding a slope (gradient) keeps unchanged the vertical time differences and therefore maintains the required modulation. It is to be noted that flat trajectory segments (top-left) are a typical indication of an infinite leaf tip speed.

In the constrained optimization of (P) all possible static (minimum leaf gap, minimum leaf tip inter-digitation, jaws movement constraints, etc.) and dynamic (minimum/maximum fluence rate, maximum gantry speed change, etc.) machine limitations are to be enforced if it is to be ensured that fully feasible trajectories are returned. Such constrained problem could be very intractable due to its enormous amount of constraints.

It is an aspect of the present invention, rather than providing a set of optimal and fully deliverable arc openings, to provide a first set of regular and smoothly changing "quasi-deliverable" binary masks/segment openings that can be used to initialize a subsequent VMAT refinement where all dosimetric and mechanical constraints are finally taken into account.

Figure 5:
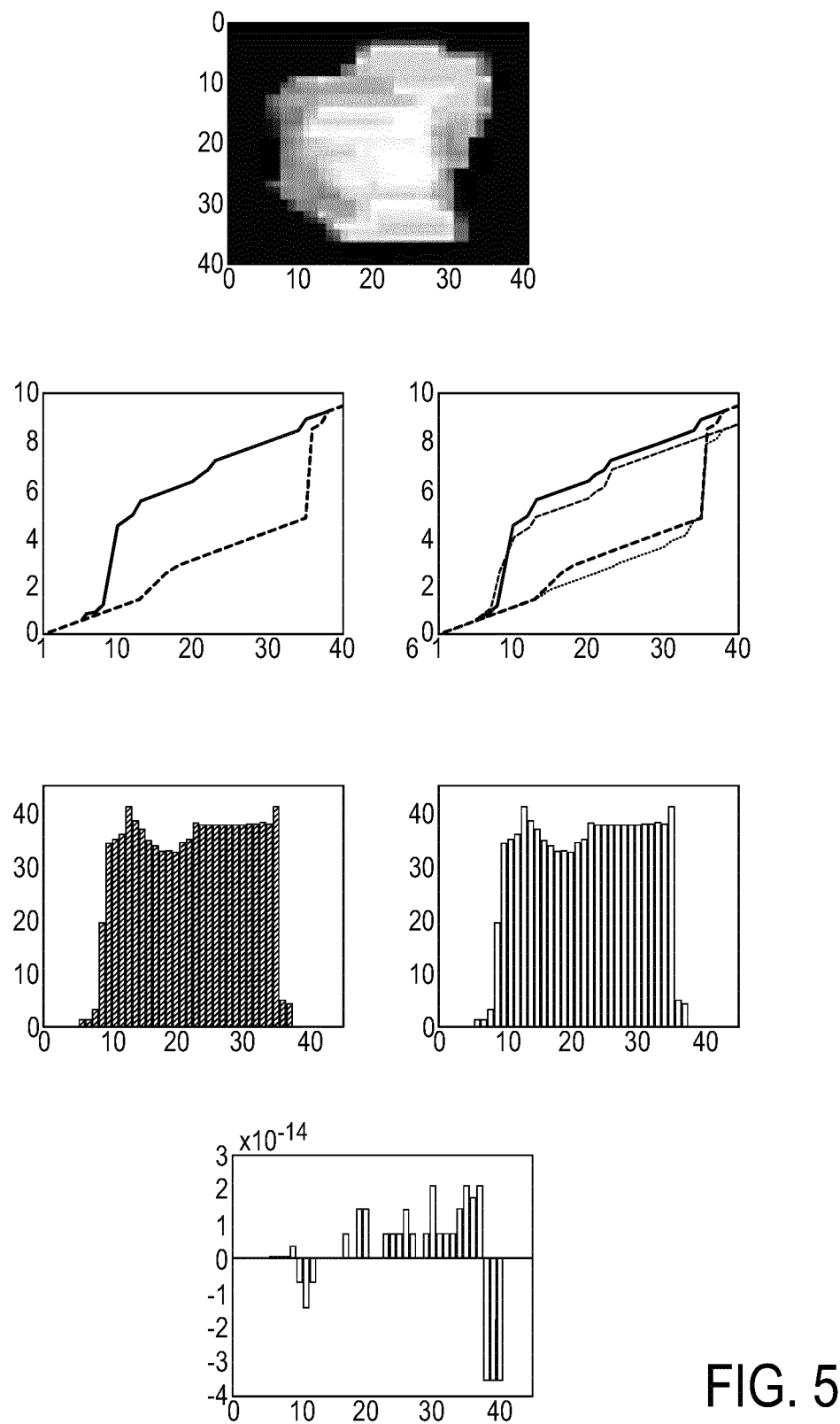
FIG. 5 illustrates a 2D example of optimal trajectories computed solving the constrained problem at (P)

FIG. 5 illustrates a 2D example of optimal trajectories computed solving the constrained problem at (P), wherein specifically, on top: the fluence map, second from top: the trajectory at 10-th row (left) and the trajectories at row 10 and 11 (right) are shown (bixel as abscissa and time as ordinate). Second from the bottom of FIG. 5 the fluence map profile at row 10 (left), the modelled profile at row 10 (right), with the the absolute error (at the bottom of FIG. 5) are given (bixel as abscissa and monitor units as ordinate).

As shown in FIG. 5 (second from top-right), different leaf pairs could sweep over the corresponding fluence map profile rows using different travel times. This happens because different fluence map rows present different level of profile complexity that would require shorter or longer leaf tip delays to exactly reach specific MU values to deliver at every bixel position. In the present embodiment, it is provided to perform a post-processing travel time normalization such that all leaf pair will sweep their profile using the very same amount of time. Here, after solving the problem at (P), first the slowest MLC leaf pair with the longest travel time $t^{slow}$ is identified, and secondly the slope of all other leaf pair trajectories are normalized such that all leaf pairs will sweep the 2D fluence profile using the very same amount of time $t^{slow}$ (see FIG. 6, discussed below):

$$t^l_{i,j} = t^l_{i,j} + \frac{j}{NCols}(t^{slow} - t^l_{i,NCols})$$

$$t^r_{i,j} = t^r_{i,j} + \frac{j}{NCols}(t^{slow} - t^r_{i,NCols})$$

Figure 6:
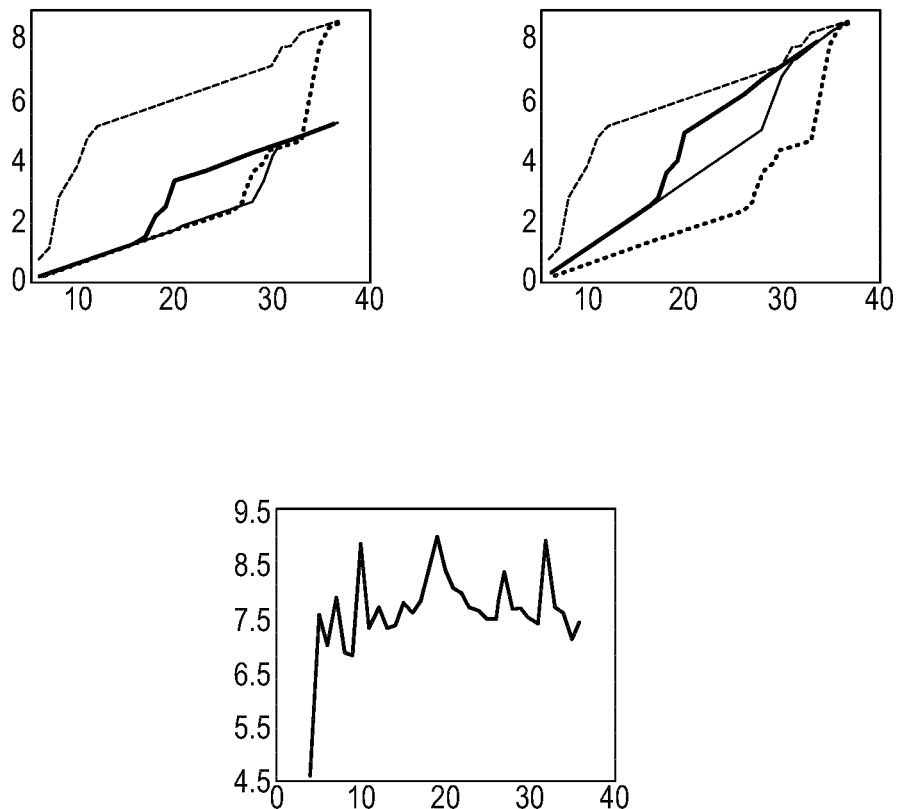
FIG. 6 shows optimized and normalized trajectories together with normalized leaf speeds.

FIG. 6 shows optimized (top left) and corresponding normalized trajectories (top right) for the fluence map rows (i.e. MLC leaf pairs) 4 and 19 (bixel as abscissa and time as ordinate), and the final normalized leaf speeds for all MLC leaf pairs (bottom, leaf number as abscissa and speed (in bixel/s) as ordinate).

It may be stressed that such time-normalization as discussed above will not increase the total treatment time for the current fluence map delivery. Below, it will be shown that such trajectory time normalization is beneficial to produce binary masks with much more regular shapes contours.

As indicated above, a calculation step 30 follows the optimization step 20 and the normalization step 25.

In the present embodiment, the calculation step 30 provides a warm start segment openings (binary masks) computation.

During inverse planning for VMAT, the MLC segment openings (as known as "control points") are computed for each arc point (control point) that needs to be delivered. As already discussed above, the VMAT planning optimization starts with the optimization of fluence maps at different arc subsectors. For each of these N fluence maps a user-defined number of initial segment openings $N_{cp}$ will be computed via an arc opening generation method. These $N \cdot N_{cp}$ openings will cover the whole VMAT arc to be delivered. Finally, multiple arc openings refinement and dose optimization steps can be executed iteratively to further improve the set of initial segments openings (and their corresponding MU values) till a user required dose quality is reached.

In the present embodiment, a sliding window technique is provided to compute an initial quasi-deliverable set of segment openings (binary masks) to smartly initialize a subsequent VMAT refinement algorithm.

For each fluence map $I_k$ computed with steps 10 and 15, in the normalization step 25, a set of time-normalized trajectories is computed using the method as discussed above for step 20. Here, the total trajectory travel time $t^{slow}$ is split on $N_{cp}$ equally-spaced time intervals $dt_n$, n=0, ..., $N_{cp-1}$. Finally, a binary mask (as referred to as "stripe") is computed for each time interval $dt_n$.

Figure 7:
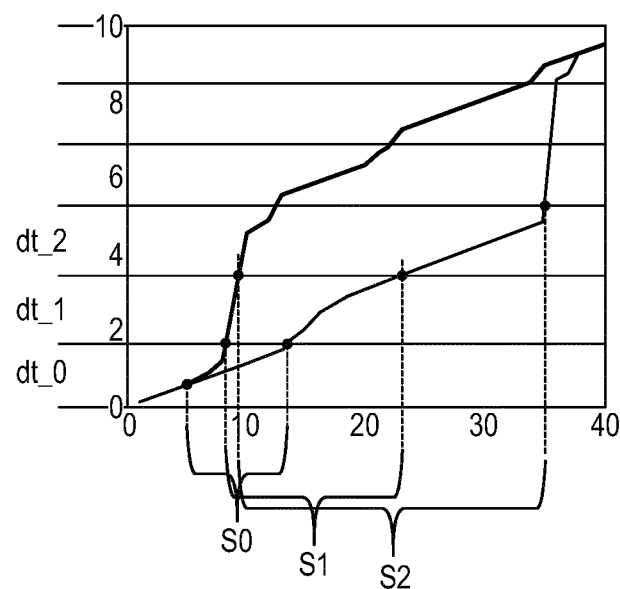
FIG. 7 illustrates trajectories time intervals computation and corresponding computed binary masks.
Figure 7:
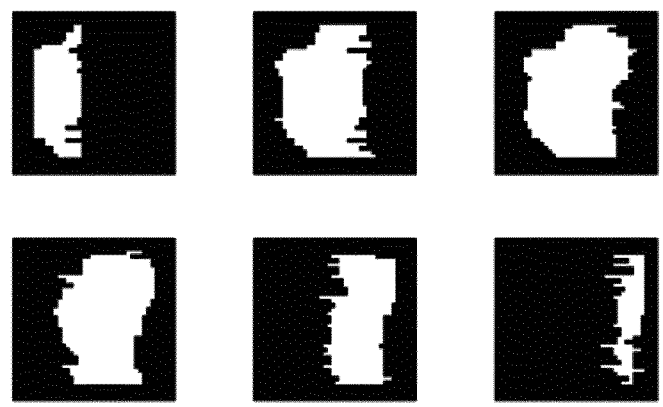

FIG. 7 illustrates trajectories time intervals computation (top; bixel as abscissa and time as ordinate; S0, S1 and S2 illustrating stripes) and corresponding computed binary masks ("stripes") (bottom). For each time interval dt a binary mask is computed. Here, a binary mask element is set to 1 if and only if the corresponding bixel was exposed by the right leaf tip and was not covered by the corresponding left tip in the previous time intervals, while it is set to zero otherwise. In other words, for a binary mask at the time interval $dt_n$, n=0, ..., $N_{cp-1}$ a mask element at position (i,j) is set to 1 if and only if the corresponding bixel at position (i,j) was exposed by the right leaf tip and was not covered by the corresponding left tip during the previous time interval [0, $dt_{n-1}$], while it is set to zero otherwise.

Figure 8:
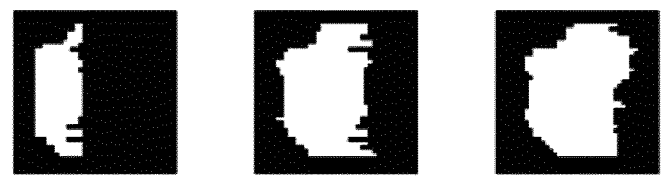
FIG. 8 illustrates binary masks computed without and with leaf tips trajectories time normalization.
Figure 8:
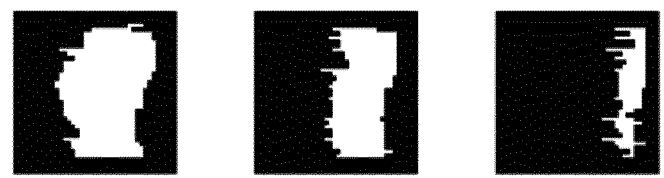
Figure 8:
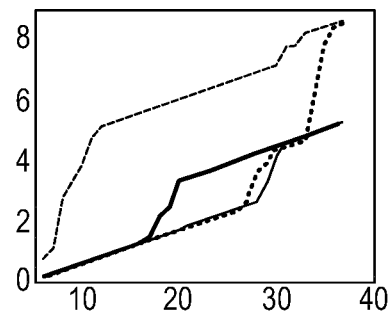
Figure 8:
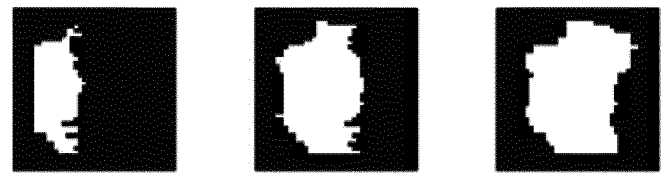
Figure 8:
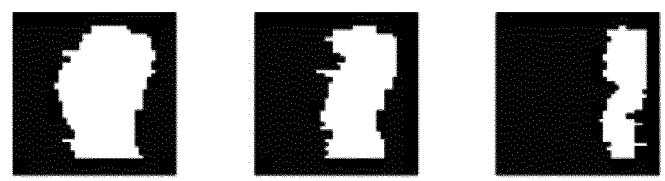
Figure 8:
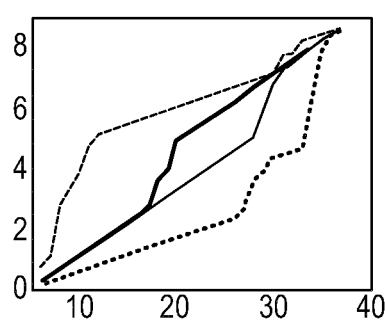
Figure 8:
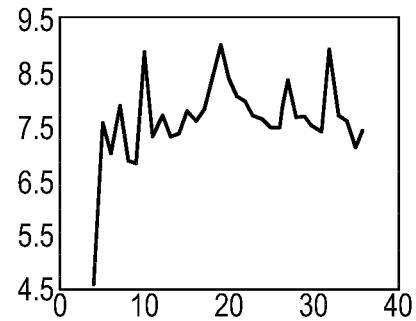

FIG. 8 illustrates binary masks computed without (top three lines) and with (bottom three lines) leaf tips trajectories time normalization. From FIG. 8 it can be seen that trajectories time-normalization can improve the regularity and smoothness of the generated binary masks.

Figure 9:
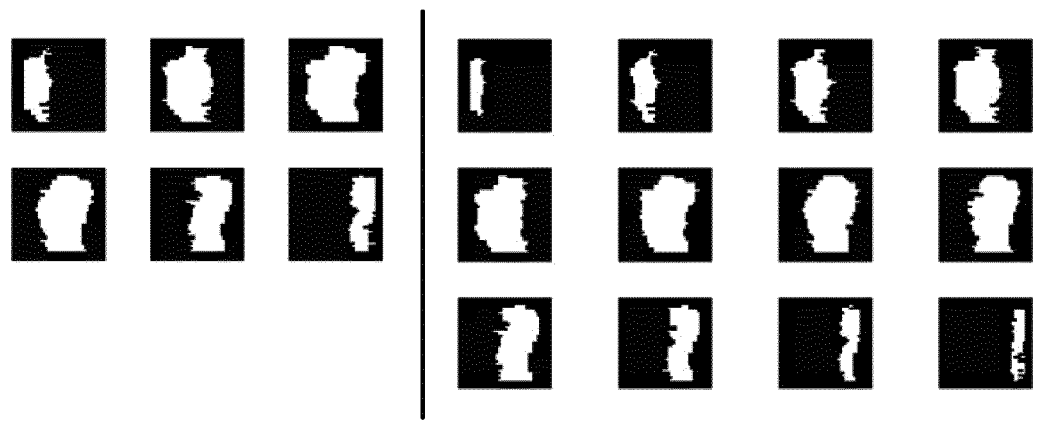
FIG. 9 shows computed binary masks using 6 and 12 segment openings per each fluence map.

FIG. 9 shows computed binary masks using 6 (left) and 12 (right) segment openings (control points) per each fluence map, while it can be seen that increasing the number of control points does not reduce the size of the stripes and that new openings look interconnected to each other. This means that increasing the number of arc points (control points) will reduce neither the binary masks shape size nor their regularity.

Figure 10:
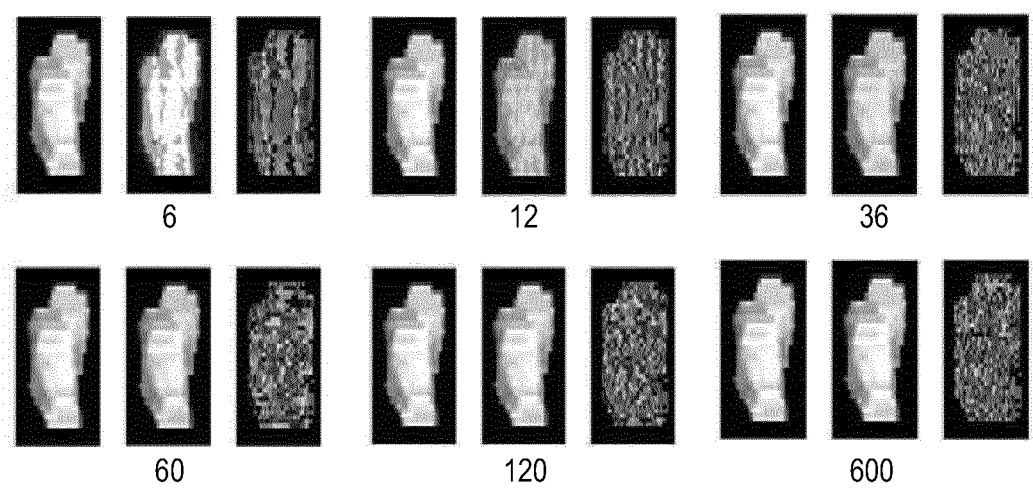
FIG. 10 illustrates dynamic leaf sweeping performances using different sets binary masks to sequence a fluence map.

FIG. 10 illustrates dynamic leaf sweeping performances using a set of 6, 12, 36, 60, 120, 600 binary masks to sequence a fluence map. For each set the ideal (left), the modelled (middle) and the absolute difference (right) fluence map images are given. In FIG. 10, the sequencing accuracy of the proposed striping routine is shown assuming a constant dose rate is used over the whole VMAT arc. It can be seen that increasing the number of control points per fluence map (i.e. reducing the arc points angular spacing) can help to improve the leaf sequencing modelling power enormously.

Figure 11:
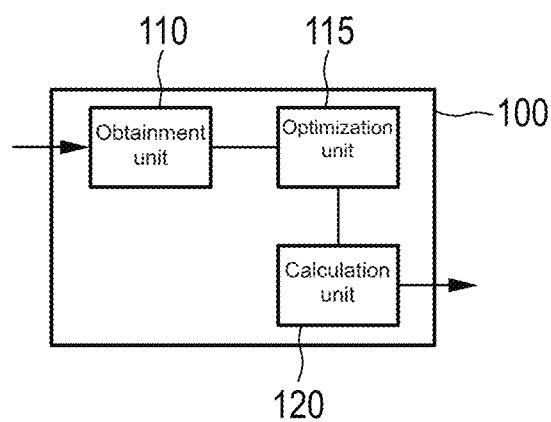
FIG. 11 shows a device for generating an input for an optimization of a volumetric modulated arc therapy plan for a multileaf collimator according to an embodiment of the invention.

FIG. 11 shows a device for generating an input for an optimization of a volumetric modulated arc therapy plan for a multileaf collimator according to an embodiment of the invention. The device 100 includes an information obtainment unit 110, an optimization unit 115, and a calculation unit 120.

The information obtainment unit 110 obtains information indicative of a desired dosage and/or intensity distribution. As discussed above, with regard to the method aspect, the input may be desired dosage, wherein the information obtainment unit then furthermore generates resampled fluence maps fitting the specific linac MLC gird and provides these to the optimization unit 115.

The optimization unit 115 solves, for each of a plurality of arc angular sectors, a constrained optimization problem, so to obtain leaf tip trajectories reflecting the desired dosage and/or intensity distribution, the constraints including constraints as to an energy source, static constraints as to the multileaf collimator and/or dynamic constraints as to the multileaf collimator. This solving may also be followed by a normalization. In any case, the results are provided to the calculation unit 120.

The calculation unit 120 calculates, for each of the plurality of the arc angular sections, a binary mask indicating exposure of bixels by the multileaf collimator and makes available the plurality of binary masks as input for the optimization of the volumetric modulated arc therapy plan.

The units discussed may be incorporated, in total or in part, into a single processor.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like obtaining information, solving optimization problems or optimizing, calculating and processing data can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A computer-implemented method of generating an input for an optimization of an external beam radiotherapy plan for a multileaf collimator, the computer-implemented method comprising:
   obtaining information indicative of a desired dosage and/or an intensity distribution;
   solving, for each arc angular sector of a plurality of arc angular sectors a constrained optimization problem to obtain leaf tip trajectories or leaf tip positions reflecting the desired dosage and/or the intensity distribution, wherein constraints of the constrained optimization problem include static constraints and/or dynamic constraints as to the multileaf collimator;
   calculating a plurality of binary masks for the plurality of the arc angular sectors, respectively, each binary mask of the plurality of binary masks indicating an exposure of bixels by the multileaf collimator; and
   providing the plurality of binary masks as an input for the optimization of the external beam radiotherapy plan.

2. The computer-implemented method according to claim 1, wherein the external beam radiotherapy plan comprises a volumetric modulated arc therapy, the computer-implemented method further comprising:
   normalizing the leaf tip trajectories to a travel time.

3. The computer-implemented method according to claim 1, wherein the constrained optimization problem comprises a least-square optimization problem.

4. The computer-implemented method according to claim 1, wherein obtaining the information indicative of the desired dosage and/or the intensity distribution includes obtaining and de-noising a target fluence map.

5. The computer-implemented method according to claim 1, wherein the external beam radiotherapy plan comprises a volumetric modulated arc therapy and the leaf tip trajectories comprise unidirectional moving trajectories.

6. The computer-implemented method according to claim 1, wherein the external beam radiotherapy plan comprises a volumetric modulated arc therapy, and wherein the constraints of the constrained optimization problem include limits as to one or more slopes of the leaf tip trajectories, an avoidance of leaf tip crashing, a minimum leaf gap, a minimum leaf tip inter-digitation, jaws movement, a fluence rate, and/or a gantry speed.

7. The computer-implemented method according to claim 1, wherein the external beam radiotherapy plan comprises a volumetric modulated arc therapy, and wherein solving, for each arc angular sector of the plurality of arc angular sectors, the constrained optimization problem comprises setting initial leaf tip trajectories to zero.

8. The computer-implemented method according to claim 1, further comprising:
generating the plurality of binary masks for an optimization of the external beam radiotherapy plan.

9. The computer-implemented method according to claim 1, wherein the constraints of the constrained optimization problem further include constraints as to an energy source.

10. A device for generating an input for an optimization of an external beam radiotherapy plan for a multileaf collimator, comprising:
a processor; and
a non-transitory medium for storing instructions, that when executed by the processor, cause the processor to:
obtain information indicative of a desired dosage and/or an intensity distribution;
solve a constrained optimization problem for each arc angular sector of a plurality of arc angular sectors to obtain leaf tip trajectories or leaf tip positions reflecting the desired dosage and/or the intensity distribution, wherein constraints of the constrained optimization problem include static constraints and/or dynamic constraints as to the multileaf collimator;
calculate a plurality of binary masks for the plurality of the arc angular sectors, respectively, each binary mask of the plurality of binary masks indicating an exposure of bixels by the multileaf collimator; and
provide the plurality of binary masks as an input for the optimization of the external beam radiotherapy plan.

11. The device of claim 10, wherein the external beam radiotherapy plan comprises a volumetric modulated arc therapy, and wherein the instructions further cause the processor to:
normalize the leaf tip trajectories to a travel time.

12. The device of claim 10, wherein the constrained optimization problem comprises a least-square optimization problem.

13. The device of claim 10, wherein the instructions further cause the processor to:
obtain the information indicative of the desired dosage and/or the intensity distribution by obtaining and denoising a target fluence map.

14. The device of claim 10, wherein the external beam radiotherapy plan comprises a volumetric modulated arc therapy and the leaf tip trajectories comprise unidirectional moving trajectories.

15. The device of claim 10, wherein the external beam radiotherapy plan comprises a volumetric modulated arc therapy, and wherein the constraints of the constrained optimization problem include limits as to one or more slopes of the leaf tip trajectories, an avoidance of leaf tip crashing, a minimum leaf gap, a minimum leaf tip inter-digitation, jaws movement, a fluence rate, and/or a gantry speed.

16. The device of claim 10, wherein the external beam radiotherapy plan comprises a volumetric modulated arc therapy, and wherein the instructions further cause the processor to:
solve the constrained optimization problem for each arc angular sector of the plurality of arc angular sectors by setting initial leaf tip trajectories to zero.

17. The device of claim 10, wherein the instructions further cause the processor to:
generate the plurality of binary masks for an optimization of the external beam radiotherapy plan.

18. A non-transitory computer readable medium that stores instructions that, when executed by a processor, cause the processor to:
obtain information indicative of a desired dosage and/or an intensity distribution;
solve a constrained optimization problem for each arc angular sector of a plurality of arc angular sectors to obtain leaf tip trajectories reflecting the desired dosage and/or the intensity distribution, wherein constraints of the constrained optimization problem include static constraints and/or dynamic constraints as to a multileaf collimator;
calculate a plurality of binary masks for the plurality of the arc angular sectors, respectively, each binary mask of the plurality of binary masks indicating an exposure of bixels by the multileaf collimator; and
provide the plurality of binary masks as an input for an optimization of an external beam radiotherapy plan for the multileaf collimator.

19. The non-transitory computer readable medium of claim 18, wherein the constrained optimization problem comprises a least-square optimization problem.

20. The non-transitory computer readable medium of claim 18, wherein the instructions further cause the processor to:
obtain the information indicative of the desired dosage and/or the intensity distribution by obtaining and denoising a target fluence map.

* * * * *